United States Patent
Borowsky

(10) Patent No.: US 8,579,984 B2
(45) Date of Patent: Nov. 12, 2013

(54) SHOULDER JOINT REPAIR

(76) Inventor: Keith Borowsky, Maidstone (GB)

(*) Notice: Subject to any disclaimer, the term of this patent is extended or adjusted under 35 U.S.C. 154(b) by 0 days.

(21) Appl. No.: 13/380,572

(22) PCT Filed: May 28, 2010

(86) PCT No.: PCT/GB2010/050911
§ 371 (c)(1),
(2), (4) Date: Apr. 5, 2012

(87) PCT Pub. No.: WO2010/149989
PCT Pub. Date: Dec. 29, 2010

(65) Prior Publication Data
US 2012/0191202 A1 Jul. 26, 2012

(30) Foreign Application Priority Data
Jun. 23, 2009 (GB) .................................. 0910821.8

(51) Int. Cl.
A61F 2/40 (2006.01)

(52) U.S. Cl.
USPC ...................................................... 623/19.14

(58) Field of Classification Search
USPC ............... 623/19.11–19.14, 20.11–20.15, 623/22.11–22.15, 22.4–22.46, 23.11–23.15
See application file for complete search history.

(56) References Cited

U.S. PATENT DOCUMENTS

| | | | |
|---|---|---|---|
| 3,979,778 A | 9/1976 | Stroot | |
| 4,045,825 A | 9/1977 | Stroot | |
| 4,605,416 A * | 8/1986 | Grobbelaar | 623/23.27 |
| 4,988,351 A | 1/1991 | Paulos | |
| 5,197,989 A * | 3/1993 | Hinckfuss et al. | 623/22.42 |
| 5,324,291 A * | 6/1994 | Ries et al. | 606/71 |
| 5,665,088 A * | 9/1997 | Gil et al. | 606/74 |
| 5,797,916 A * | 8/1998 | McDowell | 606/74 |
| 5,941,881 A * | 8/1999 | Barnes | 606/71 |
| 5,944,758 A | 8/1999 | Mansat | |
| 6,066,141 A * | 5/2000 | Dall et al. | 606/74 |
| 6,127,596 A * | 10/2000 | Brown et al. | 623/16.11 |
| 6,171,341 B1 * | 1/2001 | Boileau et al. | 623/19.11 |
| 6,221,107 B1 * | 4/2001 | Steiner et al. | 623/13.14 |

(Continued)

FOREIGN PATENT DOCUMENTS

DE 102007014267 A1 10/2008
EP 0358372 A1 3/1990

(Continued)

OTHER PUBLICATIONS

GB search report in GB 0910821.8, dated Sep. 14, 2009.

(Continued)

*Primary Examiner* — Alvin J. Stewart
(74) *Attorney, Agent, or Firm* — Blakely Sokoloff Taylor & Zafman

(57) ABSTRACT

A shoulder joint repair prosthesis (12, 14) comprises a support structure which comprises anchorage points (24) which are in the installed configuration positioned adjacent positions of the anatomical tendinous insertion points of the tendons related to the joint. A securing clamp (30) arrangement connects to the anchorage points with direct rigid connection devices (32), the securing clamp arrangement having a surface area larger than the direct connection devices, the securing clamp arrangement being arranged to clamp the tendons between the securing clamp arrangement and the underlying surface area and providing a fixed gap between clamp and underlying connecting areas to trap any attached bony fragments.

12 Claims, 12 Drawing Sheets

(56) References Cited

U.S. PATENT DOCUMENTS

| | | | |
|---|---|---|---|
| 6,338,734 B1* | 1/2002 | Burke et al. | 606/281 |
| 6,398,812 B1* | 6/2002 | Masini | 623/19.14 |
| 6,558,425 B2* | 5/2003 | Rockwood, Jr. | 623/19.12 |
| 6,592,622 B1* | 7/2003 | Ferguson | 623/13.14 |
| 6,799,380 B2* | 10/2004 | Afriat | 33/562 |
| 7,001,429 B2* | 2/2006 | Ferguson | 623/13.14 |
| 7,175,664 B1 | 2/2007 | Lakin | |
| 7,179,259 B1* | 2/2007 | Gibbs | 606/64 |
| 7,207,993 B1* | 4/2007 | Baldwin et al. | 606/70 |
| 7,435,263 B2* | 10/2008 | Barnett et al. | 623/19.12 |
| 7,476,253 B1* | 1/2009 | Craig et al. | 623/19.14 |
| 7,517,364 B2* | 4/2009 | Long et al. | 623/19.14 |
| 7,556,652 B2* | 7/2009 | Angibaud et al. | 623/19.14 |
| 7,608,109 B2* | 10/2009 | Dalla Pria | 623/19.11 |
| 8,105,385 B2* | 1/2012 | Maroney et al. | 623/19.14 |
| 8,118,868 B2* | 2/2012 | May et al. | 623/13.14 |
| 8,252,061 B2* | 8/2012 | Mikami et al. | 623/23.15 |
| 8,308,806 B2* | 11/2012 | Grant et al. | 623/19.14 |
| 2001/0011193 A1* | 8/2001 | Nogarin | 623/19.14 |
| 2002/0151982 A1* | 10/2002 | Masini | 623/19.14 |
| 2002/0183849 A1* | 12/2002 | Grusin et al. | 623/19.14 |
| 2003/0014119 A1* | 1/2003 | Capon et al. | 623/19.11 |
| 2003/0028253 A1* | 2/2003 | Stone et al. | 623/19.14 |
| 2003/0171816 A1* | 9/2003 | Scifert et al. | 623/22.12 |
| 2004/0006392 A1* | 1/2004 | Grusin et al. | 623/19.14 |
| 2004/0034431 A1* | 2/2004 | Maroney et al. | 623/19.14 |
| 2004/0064187 A1* | 4/2004 | Ball et al. | 623/19.14 |
| 2004/0143335 A1* | 7/2004 | Dews et al. | 623/19.14 |
| 2004/0153161 A1* | 8/2004 | Stone et al. | 623/19.14 |
| 2004/0230311 A1* | 11/2004 | Cyprien et al. | 623/19.11 |
| 2004/0236337 A1* | 11/2004 | Deloge et al. | 606/74 |
| 2004/0236373 A1 | 11/2004 | Anspach | |
| 2005/0060040 A1 | 3/2005 | Auxepaules | |
| 2005/0071014 A1* | 3/2005 | Barnett et al. | 623/19.14 |
| 2005/0085919 A1* | 4/2005 | Durand-Allen et al. | 623/19.11 |
| 2005/0090902 A1* | 4/2005 | Masini | 623/19.14 |
| 2005/0177241 A1 | 8/2005 | Angibaud | |
| 2005/0288681 A1* | 12/2005 | Klotz et al. | 606/102 |
| 2006/0009852 A1* | 1/2006 | Winslow et al. | 623/19.14 |
| 2006/0041261 A1 | 2/2006 | Osypka | |
| 2006/0149266 A1 | 7/2006 | Cordasco | |
| 2006/0276903 A1* | 12/2006 | Maroney et al. | 623/19.14 |
| 2007/0129809 A1* | 6/2007 | Meridew et al. | 623/22.32 |
| 2007/0142918 A1* | 6/2007 | Stone | 623/19.13 |
| 2007/0156246 A1* | 7/2007 | Meswania et al. | 623/19.12 |
| 2007/0179625 A1* | 8/2007 | Ekholm et al. | 623/19.14 |
| 2007/0244565 A1* | 10/2007 | Stchur | 623/19.14 |
| 2007/0260321 A1* | 11/2007 | Stchur | 623/19.11 |
| 2007/0265704 A1 | 11/2007 | Mayer | |
| 2008/0177393 A1* | 7/2008 | Grant et al. | 623/18.11 |
| 2008/0234829 A1* | 9/2008 | Mutchler et al. | 623/19.14 |
| 2008/0281428 A1* | 11/2008 | Meyers et al. | 623/20.35 |
| 2009/0118734 A1 | 5/2009 | Bhatnagar | |
| 2009/0265010 A1* | 10/2009 | Angibaud et al. | 623/19.11 |
| 2010/0057210 A1* | 3/2010 | Ondrla | 623/19.14 |
| 2010/0076561 A1* | 3/2010 | Emmanuel | 623/19.11 |
| 2010/0292802 A1* | 11/2010 | Borowsky | 623/19.14 |
| 2011/0029089 A1* | 2/2011 | Giuliani et al. | 623/19.14 |
| 2011/0054623 A1* | 3/2011 | Ferko | 623/19.14 |
| 2011/0082557 A1* | 4/2011 | Mutchler et al. | 623/19.14 |
| 2011/0178604 A1* | 7/2011 | Porter | 623/19.14 |
| 2012/0290098 A1* | 11/2012 | Mutchler et al. | 623/19.14 |
| 2012/0303130 A1* | 11/2012 | Winslow et al. | 623/19.12 |
| 2012/0310360 A1* | 12/2012 | Parrott et al. | 623/19.14 |
| 2012/0330428 A1* | 12/2012 | Splieth et al. | 623/19.14 |
| 2013/0006369 A1* | 1/2013 | Wiley et al. | 623/19.14 |

FOREIGN PATENT DOCUMENTS

| | | |
|---|---|---|
| EP | 1269941 A | 1/2003 |
| EP | 1943985 A1 | 7/2008 |
| FR | 2880793 | 7/2006 |
| GB | 1524785 A | 9/1978 |
| GB | 2440911 | 1/2003 |
| WO | WO-99/44546 A1 | 9/1999 |
| WO | WO-2006/074413 A2 | 7/2006 |
| WO | WO-2008-020161 A1 | 2/2008 |

OTHER PUBLICATIONS

GB search report in GB0616134.3, dated Mar. 27, 2007.

* cited by examiner

SHOULDER JOINT REPAIR

FIELD OF THE INVENTION

This invention relates to apparatus for use in surgery for the purposes of joint repair, in particular a joint prosthesis.

BACKGROUND OF THE INVENTION

Muscles in the human body converge into sinew like structures (tendons) that then insert into bone. Generally this mechanism is applied across a fulcrum or joint.

In many cases, the lever arm or fulcrum involved is very short, yet the load is high. Therefore the pull that is exerted on tendons can well be several times the body weight.

This mechanism above pertains to many regions of the body, and its repair can be challenging. Ideally joints should be kept moving whilst the repair takes effect. However it can take several months for the repair process to have enough strength for normal use.

The shoulder is a more unusual example of the above because some of the muscle-tendon units are cardinal to supplying the fulcrum, not only torque. In the shoulder, the socket portion is flat and does not as much restrain the humeral head by virtue of the shape, as for sockets elsewhere in the body. The series of muscles immediately adjacent to the joint, called the rotator cuff, wrap round the humeral head and by contracting provide a type of soft tissue socket.

Musculo tendinous units may fail in several ways. Amongst these, and in the shoulder in particular, degenerative tearing of the rotator cuff tendons is common, particularly in middle age and above.

A second way in which the units fail is by fracture of the bones to which the tendons attach. The common presentation of this was described by Charles Neer as 3 and 4 part fractures of the shoulder. Such fractures may be repaired by fixation of the fragments—particularly in the younger age groups.

Sometimes and particularly in the elderly, the bone quality is so poor that fixation of the fragments and fractured humeral head is unlikely to succeed, as the screws will have no hold. In these cases the humeral head may be excised and replaced with a hemi arthroplasty (a replacement of only the ball portion of the humeral head).

A conventional prosthesis comprises a head and a stem, and the head of the prosthesis corresponds in shape to the humeral head, in particular the cartilage surface of the humeral head. The stem of the prosthesis is inserted into the top of the humerus shaft, and it is known to provide connection points at the top of the prosthesis stem which enable the greater and lesser tuberosities to be secured to the prosthesis.

The tuberosities are conventionally secured using sutures which are connected to the interface between the tuberosity bone (which has been fractured and come away from the humeral head) and the attached tendon.

There are a number of different ways to secure the tuberosities to the prosthesis. Generally, these methods use a combination of cerclage connections (in which a suture coupled to the tuberosity is secured around or to the shaft of the prosthesis) and longitudinal connections (in which a suture extends down the humerus from the tuberosity at the humerus head to a connection point on the humeral shaft).

A problem with the known shoulder replacement prostheses is that the positioning of the muscles and tendons in the replacement shoulder does not replicate the anatomical configuration. In other words it is difficult to position the tuberosities anatomically, as reference points for this are scant. Furthermore, movement of the tuberosities is often not sufficiently inhibited, and with rehabilitation they lose position and displace so that the tendon to joint connection is lost and the stability to the humeral head and therefore its fulcrum is lost. This leads to loss of active motion called pseudoparalysis and loss of strength.

Thus, repair of the tuberosity fragments and their attached rotator cuff tendons is difficult. Failure of this important element is common, and the result of these problems is pain or discomfort to the patient and/or a lack of mobility in the joint.

WO 2008/020161 discloses an improved shoulder replacement prosthesis which can more reliably replicate the anatomical structure. The head of the shoulder replacement prosthesis has a domed portion and a flange positioned at an end region of the domed portion. The flange has a width which varies around the domed portion, having a greater width at a part corresponding to a region of the greater tuberosity than at a part corresponding to a region of the lesser tuberosity, such that a rim of the flange away from the domed portion represents the position of the anatomical tendinous insertion points of the rotator cuff on the greater and lesser tuberosities. The flange is provided with a plurality of connection portions and associated surface area for securing the tendons attached to the tuberosities.

By dimensioning the flange appropriately, the anatomical positioning of the tendon to bone connections can be more accurately replicated. In particular, the flange acts to bridge the so-called bare area of the humeral head (the space between the cartilage surface and the greater tuberosity), an area which is not easily accounted for in conventional prostheses which purely supply a replica of the humeral cartilaginous head. The flange provides a firm immovable surface area to which connections can be made, so that the length of connections can be reduced, and the scope for movement of the tuberosities in the replacement joint is reduced.

Compared to more conventional suture systems, the length over which restraining connections are required for the tuberosities is reduced. With sutures, such lengthy spans of connection are prone to loosening and therefore failure.

The system above improves the anatomical replication but the efficacy of the connections still has room for improvement, so that there is still a need to improve the tendon connection mechanism.

SUMMARY OF THE INVENTION

According to the invention, there is provided a joint repair prosthesis, comprising:

a head for replacing the joint head and a connection shaft, wherein the head comprises a substantially domed portion and a flange positioned at an end region of the domed portion, wherein the flange has a width which varies around the domed portion such that a rim of the flange away from the domed portion represents the positions of the anatomical tendinous insertion points;

anchorage points provided on the flange to define a support structure or firm surface area which is positioned subjacent to positions representing the anatomical tendinous insertion points of the tendons; and a securing clamp arrangement which connects to the anchorage points with direct rigid connection devices, the securing clamp arrangement having a surface area larger than the connection devices, the securing clamp arrangement being arranged to clamp the tendons between the securing clamp arrangement and the underlying surface area, and bearing means for defining a spacing between the clamp arrangement and the underlying surface area, thereby to trap any attached bony fragments that are too large to slip through the spacing.

The invention essentially provides a plating system which provides secure attachment for the tendons, or the tendon-bone fragment complexes.

The anchorage points lie on a surface. The invention provides a surface area deep to the tendon (subjacent to the tendon insertion point) at or near its anatomical point of insertion, and a securing clamp superficial to the tendon to provide strong repair of musculo tendinous units. This avoids the need for sutures (which tend to dig into the tendon and do not provide good rigidity). The invention can be applied to different joints, not only the shoulder joint.

The flange can be designed from computer tomography scans of a bone. The securing clamp arrangement preferably has a surface which parallels the shape of the underlying flange, and for example has a stopper arrangement to define the desired spacing. The shaft preferably attaches to the head substantially medially.

The direct connection devices provide a rigid fixed coupling, for example they may comprise screws.

The anatomical positions are defined by a flange part of the prosthesis. This arrangement can be used for a shoulder replacement, in which the tendons (and associated muscles) comprise the rotator cuff, and they connect to greater and lesser tuberosities.

The flange part can comprise several anchorage portions, for example at least three.

Each clamp of the clamp arrangement can comprise an elongate arm shaped to correspond to the shape of the flange thereby providing a compression surface against the flange. This provides secure clamping against the flange.

Each clamp of the clamp arrangement can also comprise an extension arm which extends away from the flange, wherein the extension arms of the clamps together define a cage structure. This can be used to provide further stability to the bony fragments. The arms of the clamp arrangements can be connected together to define a shared web.

The shaft can be plastic, and the prosthesis is then a trial prosthesis. The use of a trial prosthesis is common in a joint replacement procedure, in order to enable the correct size and type of final prosthesis to be selected. The use of a trial prosthesis with a plastic shaft means that temporary connections to the shaft can be made easily, through the bone, by screwing directly into the shaft. This avoids the need for complex jigs when installing the trial prosthesis.

The invention also provides a method of manufacturing a joint repair prosthesis, comprising:
  generating a model of a bone joint from which tuberosities which attach to the tendons of the joint have been removed;
  using the model to design a head for replacing the joint head and a connection shaft, wherein the head comprises a substantially domed portion and a flange positioned at an end region of the domed portion, wherein the flange has a width which varies around the domed portion such that a rim of the flange away from the domed portion represents the positions of the anatomical tendinous insertion points;
  defining anchorage points on the flange, to define a support structure or firm surface area which is positioned subjacent to positions representing the anatomical tendinous insertion points of the tendons; and
  manufacturing:
    the prosthesis head and shaft;
    a securing clamp arrangement for connection to the anchorage points;
    direct rigid connection devices for connecting the securing clamp arrangement to the anchorage points, the securing clamp arrangement having a surface area larger than the connection devices; and
    means for defining a spacing between the clamp arrangement and the underlying surface area, for trapping any attached bony fragments that are too large to slip through the spacing.

BRIEF DESCRIPTION OF THE DRAWINGS

The invention will now be described in detail with reference to the accompanying drawings, in which.

DETAILED DESCRIPTION

Figure 1:
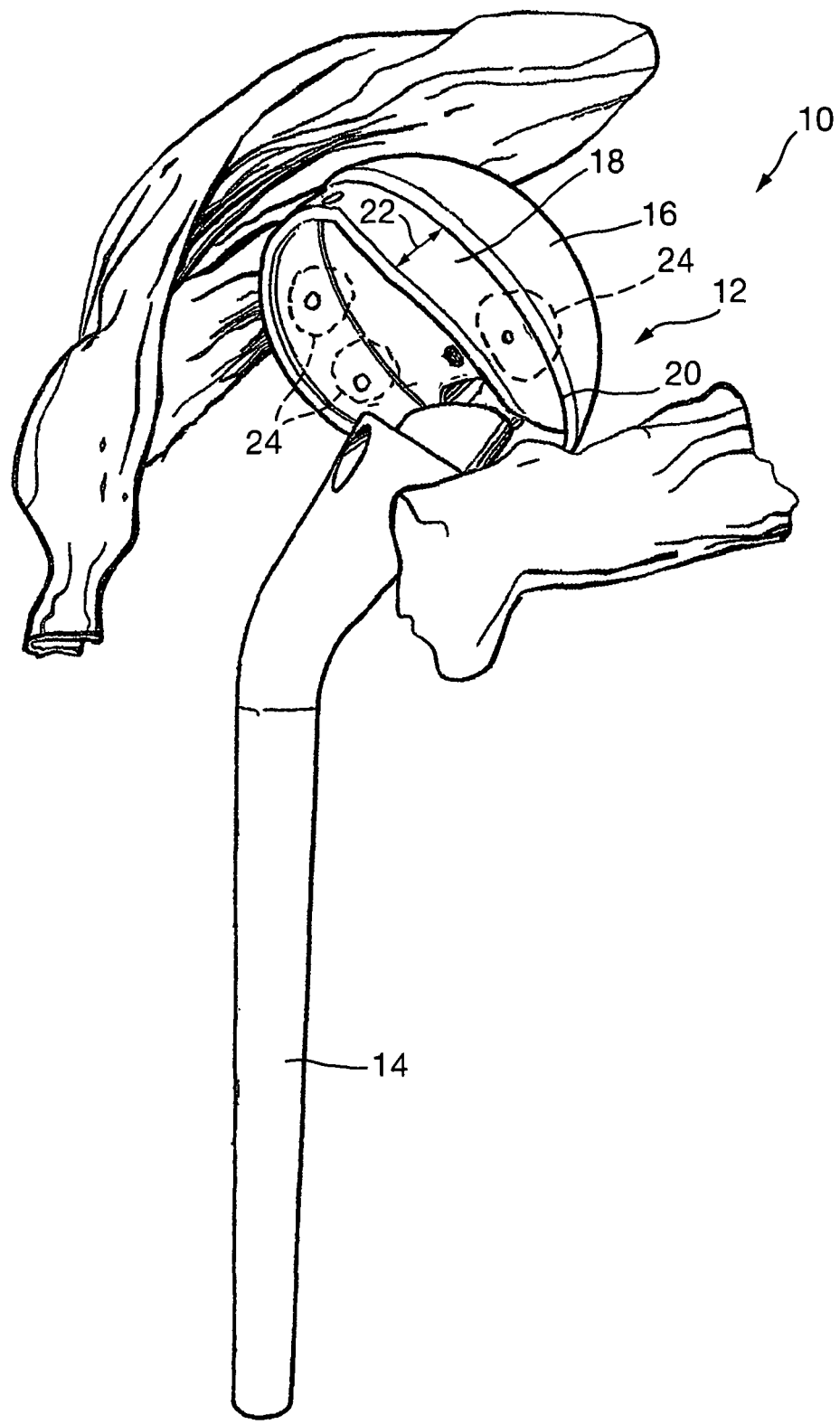
FIG. 1 shows the elements of a prosthesis for an initial explanation.

FIG. 1 shows the main components of a shoulder prosthesis, and which can be modified in accordance with the invention.

The prosthesis 10 comprises a head 12 for replacing the humeral head, and a connection shaft 14. The head has a domed portion 16 and a flange 18 extending or positioned from an end region 20 of the domed portion.

This end region 20 is the interface between the domed portion 16 and the flange 18, and may correspond to the limit of the cartilage surface of the humeral head. The end region thus defines the anatomical neck of the humeral head. The domed portion 16 corresponds in shape to the head of a conventional shoulder implant prosthesis. The shape of the end region 20 is essentially circular to oval and lies in a plane similar to what would be found anatomically, so that the domed portion has a shape which is essentially a portion of a sphere to oval defined by dissecting a sphere to oval with a plane.

The flange 18 extends or is positioned from this interface 20 and substantially defines a portion of a quasi-cylinder, which approximates the shape of insertion points of the cuff tendons into the tuberosities and the bare area. This line of insertion veers in parts substantially away from the anatomical neck. Thus, the overall outer shape of the head is of a quasi-cylinder portion which is capped with a domed portion.

The quasi-cylindrical flange 18 has a width 22 (i.e. the local length of the quasi-cylinder) which varies around its circumference. There is also an inward lip between the end of the domed portion and the flange, so that the flange may be approximately 4 mm recessed compared to the dome margin.

The flange is provided with three connection portions 24, and these are for securing the tendons attached to the tuberosities of the fractured shoulder joint.

The width 22 of the flange 18 varies, so that the flange provides a connection surface which is suitable for the tuberosity tendon to be connected to the flange at each location. Although not shown in the Figures, the positioning of the connection portions 24 along the width of the flange may also be different for the different connection portions.

One of the connection portions is for the lesser tuberosity, where there is one rotator cuff tendon connection to make, and the width of the flange may be in the range 5 mm to 8 mm or in such proportions as derived from the similar regions on cadaver specimens.

The other two connection portions are for the greater tuberosity, where there are three rotator cuff tendon connections to make, and the width of the flange is in the region of approximately 5 mm (in the range 1 mm to 8 mm) in the region of the suprapinatus tendon, gradually increasing to approximately to 12 mm (in the range 8 mm to 25 mm) at the teres minor tendon at the back (the left hand side of FIG. 1) but the precise dimensions here again are derived from cadaver specimens.

Thus, the flange has greater width at a part corresponding to a region of the greater tuberosity than at a part corresponding to a region of the lesser tuberosity.

The flange can increase uniformly in width from its minimum to its maximum (5 mm to 12 mm for the example dimensions above), and spans approximately 120 to 160 degrees.

The flange design enables the anatomical positioning of the tendon to bone connections to be more accurately replicated. In particular, the flange acts to bridge the so-called bare area of the humeral head so that the tuberosities are connected in more anatomical positions. The flange 18 provides a firm immovable surface area to which connections can be made so that the length of connections can be reduced compared to conventional suturing techniques, and the scope for movement of the tuberosities in the replacement joint is reduced.

Some of the components described above are also described in WO 2008/020161. This invention provides a modification to the way the tendons are connected to the prosthesis.

Although the shoulder will be used as an example, the system may have application in other areas of the body where tendon bone interfaces require repair or stabilisation.

FIG. 2 shows the apparatus of the invention, in outline form.

Figure 2A:
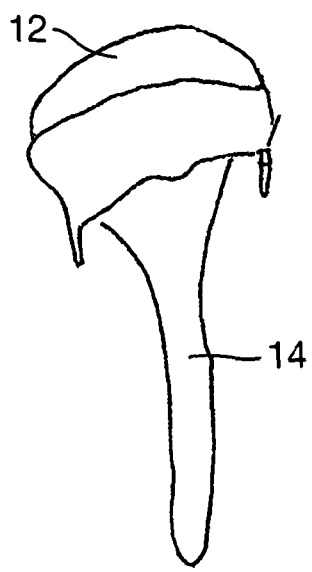
FIG. 2 shows the apparatus of the invention arranged as a prosthesis, in outline form.
Figure 2B:
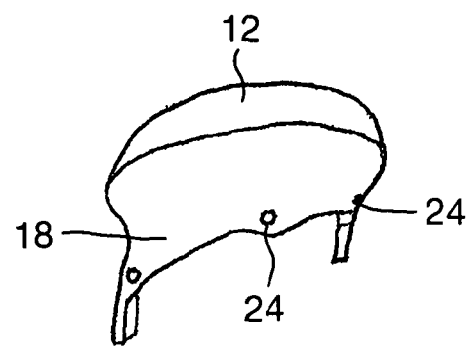

FIG. 2A shows the prosthesis having the head 12 and shaft 14. The connection points 24 shown in FIG. 2B define anchorage points, and the flange 18 with the anchorage points 24 forms a support structure. As explained above, the anchorage points are in the installed configuration positioned adjacent positions of the anatomical tendinous insertion points of the cuff of the joint.

The head with its flange is designed from cadaver specimens where the tuberosities have been removed. These specimens are computer tomographically scanned and the prosthetic flange head and shaft is derived from these scans using computer-aided design and computer-aided manufacturing.

When the tuberosities and their attached cuff tendons are laid over the flange, and the clamps are screwed down by connection devices, the tuberosities are forced to assume their anatomical positions.

Figure 2C:
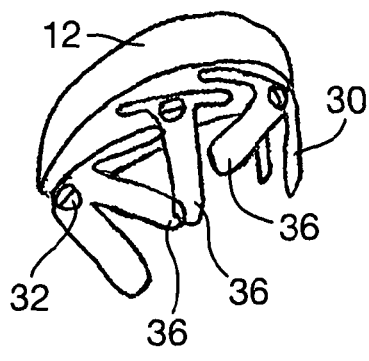

FIG. 2C shows securing clamps 30 which connect to the anchorage points 24 with direct rigid connection devices, preferably locking screws 32. The securing clamps 30 have a surface area larger than the screws so that they provide improved clamping compared to screws alone. The securing clamps 30 clamp the rotator cuff or tendons against the anchorage points.

The securing clamps 30 may be metal clamps. The locking screws 32 may be tightened in a clockwise direction to achieve the desired compression, and then turned slightly counter-clockwise, thus engaging a secondary thread on the screw head, to engage and lock the screw in the clamp.

Figure 2D:
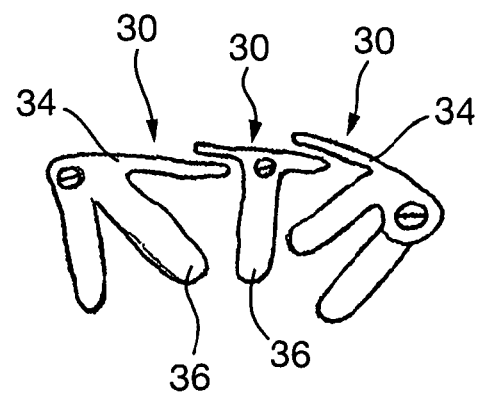

As shown in FIG. 2D, each clamp comprises an elongate arm 34 shaped to correspond to the shape of the flange to provide a compression surface against the flange. In addition, one or more extension arms 36 extends away from the flange, and these together define a cage structure.

This cage structure further contains and controls any attached bone fragments. They can be designed so that they can be moulded into shape, and linked to each other to provide further stability to the structure. The clamps can be modular (i.e. separate) as shown, or they may be formed as one piece. The number and type of rigid connections can of course vary.

Figure 3:
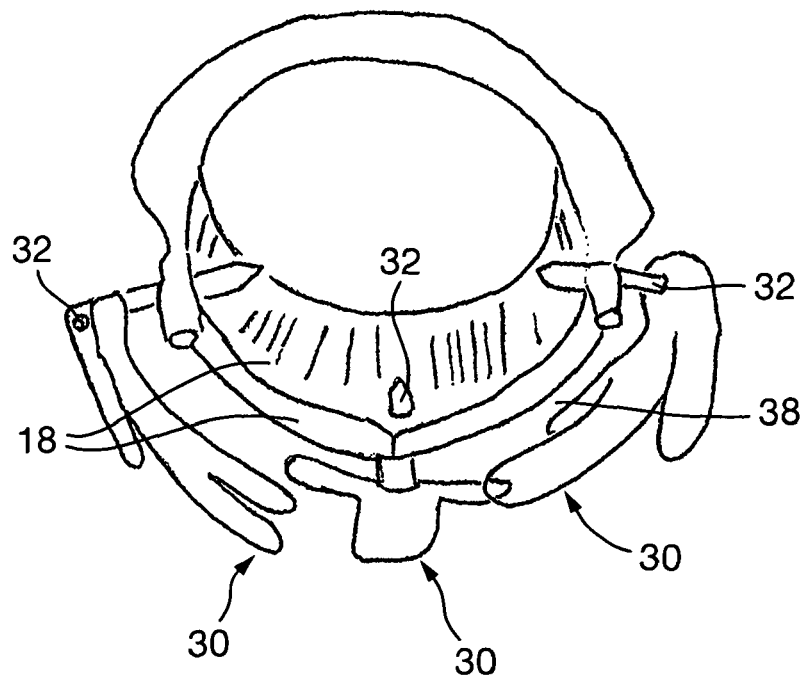
FIG. 3 shows the prosthesis of FIG. 2 from beneath.

FIG. 3 shows the prosthesis of FIG. 2 from beneath. The space in which the tendons are clamped is shown as 38. Once the connection device (screws) are tightened, this space is set by the connection device to 4 mm. In other words it is impossible to squeeze this space down to 0 mm.

Figure 4:
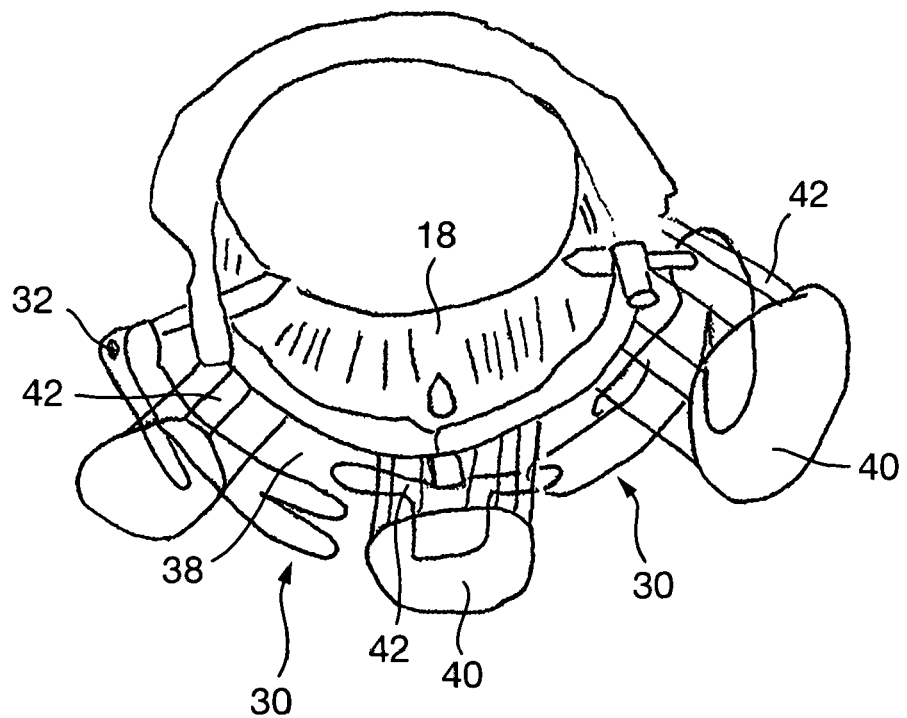
FIG. 4 adds the bone fragments and tendons to the arrangement of FIG. 3.

FIG. 4 adds the bone fragments 40 and tendons 42 to the arrangement of FIG. 3.

This system provides both compression of the tendons 42 against the surface area of the flange, and acts as a trapping mechanism for any pieces of bone 40 attached to the tendons that will be too large to slip through the space 38 between the clamp and receptive area of the flange. The design limiting the space to approximately 4 mm provides the desired trapping effect. The extensions 36 further contain and control any attached bone fragments.

The invention also provides an improved way to design the shape of the head of the prosthesis.

In particular, the flange is constructed by taking a cadaver bone, and removing the tuberosities along the line of insertion of the rotator cuff tendons into the tuberosities. The remaining piece of bone is then cat scanned (computerized axial tomography) to produce a 3 dimensional picture. The data from this scan is then fed into a cad cam (computer-aided design and computer-aided manufacturing) system that then reproduces a metallic shape of the proximal humerus (minus tuberosities) very accurately.

The remnant portions of cat scanned bone just preceding the removed tuberosities, thus represent, and are translated to, an anatomical metal flange emerging from the metal humeral head. The flange is provided with a plurality of connection portions and associated surface area for securing the tendons attached to the tuberosities.

On the cad cam system, a low profile clamp or clamps are designed parallel to and following the shape of the flange. Counter sunk sockets are created in this clamp to accommodate screws. Corresponding threads are tapped into the flange. This creates a clamp of similar shape to the flange that can be screwed down onto the flange.

A metal buffer of 4 mm is set to the under surface of the clamp, such that when the screws are tightened down, complete closure of the gap between the flange and skirt is not possible, and so that when the connecting screws are tightened, a fixed gap of 4 mm remains between clamp and skirt. This 4 mm gap may typically be between 3 mm and 6 mm. The lower limit prevents over-compression of the tendons, and the upper limit ensures trapping of the tuberosities.

The connecting screws have small secondary locking threads on their heads which engage the countersunk sockets in the clamp and prevent dislodgement of the screws when the system is jolted by repetitive motion.

In the surgical operation, the prosthesis stem is fixed in the humeral shaft with cement. The tuberosities with their attached rotator cuff tendons are then laid over the prosthetic head. As the flange is anatomically created from cat scans, the tuberosities and their attached tendons acquire an anatomical position as they are laid over the head. The clamp is then applied and screwed down over the tendons until the metal buffer engages, thus setting the clamp skirt distance to the selected distance (4 mm in this example).

At this set distance, any contraction of the tendons in an attempt to displace their tuberosities results in abutment of the tuberosities against the clamp. Effectively the tuberosities being larger than 4 mm are unable to displace as they are caught by this small gap which provides a gate or trapdoor mechanism.

The clamp has additional malleable metal extensions that are moulded around the tuberosities to further secure their hold.

The arrangement of the invention avoids the need for sutures, which tend to dig into the tendon and do not provide good rigidity. The malleable metallic extensions of the clamp can be moulded around the tuberosities to define a cage structure. This can be used to provide further stability to the bony fragments. The more immediate connection system of this design compared to sutures reduces the chance of loosening and displacement of the tuberosities.

The shaft of the prosthesis joins the prosthetic head substantially more medially than other prostheses, thus allowing for more bone graft to be placed deep to the tuberosities and augmenting therefore biological healing.

The clamp and flange, as well as the head and shaft of the prosthesis may be modular. The number of screws, the number and design of the metallic extensions etc. may vary provided they conform to the above principles. Similarly the surfaces may be coated with biological material to promote healing.

In surgery before such prostheses are finally cemented into place, so called trial versions are tried to estimate appropriate size, convenience of fit, appropriate height and rotational setting of the prosthesis and appropriate reduction of the tuberosities. Conventional trials are difficult to hold in the correct position while such tests are performed. They often are held in position by complicated jigs that interfere with estimation of tuberosity reduction and assessment of movement.

This prosthesis of the invention can have trial versions in which the stem or shaft portion is made of a disposable Ultra High Molecular Weight Polyethylene plastic. This allows a Kirschner wire to be drilled through the humeral shaft bone and through the plastic prosthetic shaft, establishing a test position for height, rotation and trial reduction of the tuberosities, without complicated and interfering jigs or securing devices that obscure vision and assessment of movement and tuberosity reduction.

Figure 5:
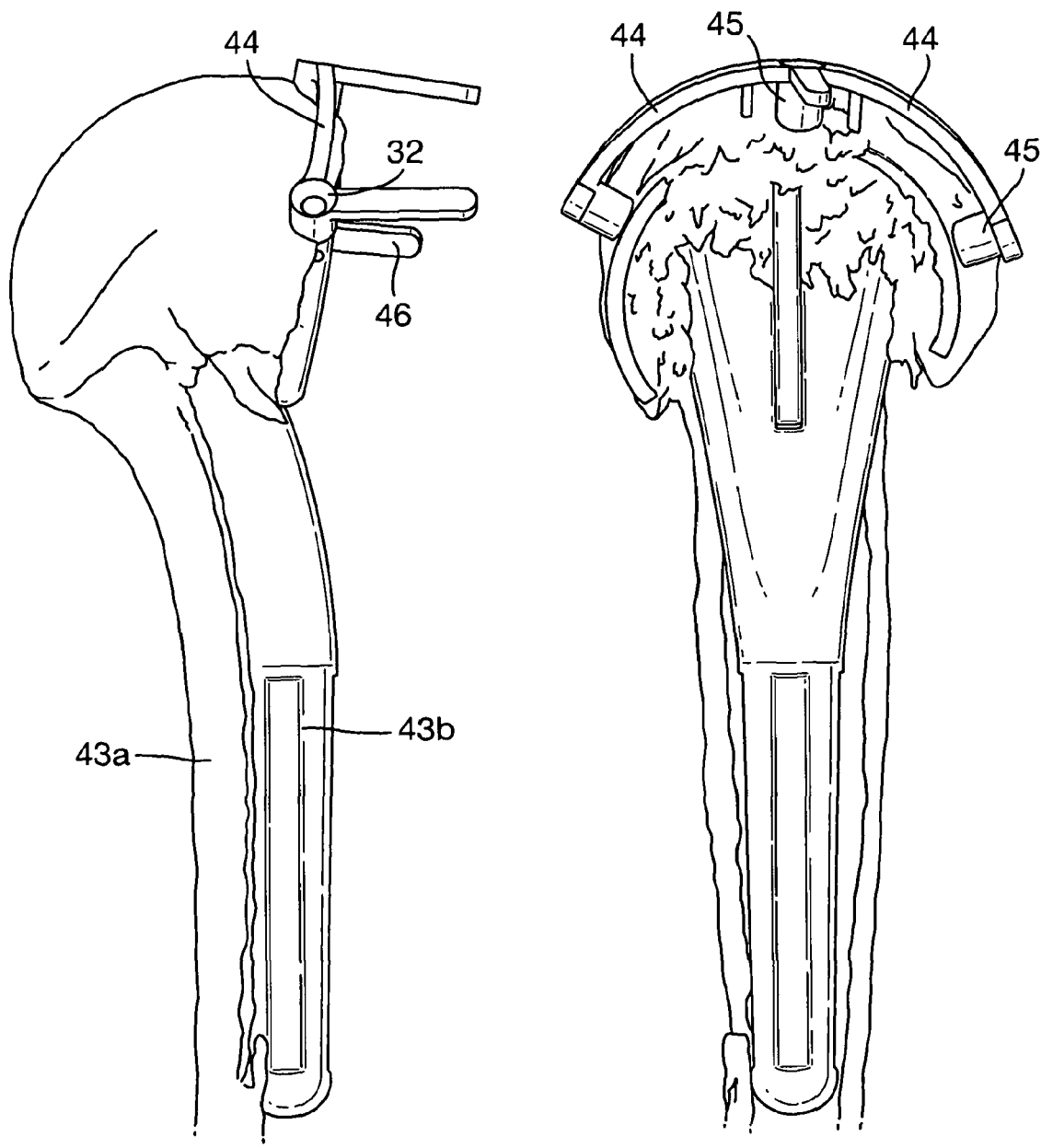
FIG. 5 shows the overlap between the design of the prosthesis and a scan of the human bone.

FIG. 5 shows the overlap between the design of the prosthesis and a scan of the human bone, The scan of the bone is used as the basis for the design of the shape of the prosthesis. For example the image part 43a is the scan of the bone and part 43b is the overlay of the prosthesis design. The head will not be a perfect dome, and will be based on the scanned bone. The securing clamps are connected together by a web 44. The web has bosses 45 which define the desired spacing at the location of the three anchors 32. However, the web 44 may be sufficiently rigid that only one boss is required for the central anchor.

Each clamp has an extending arm 46 which can be bent over the joint after the prosthesis has been fitted.

Figure 6:
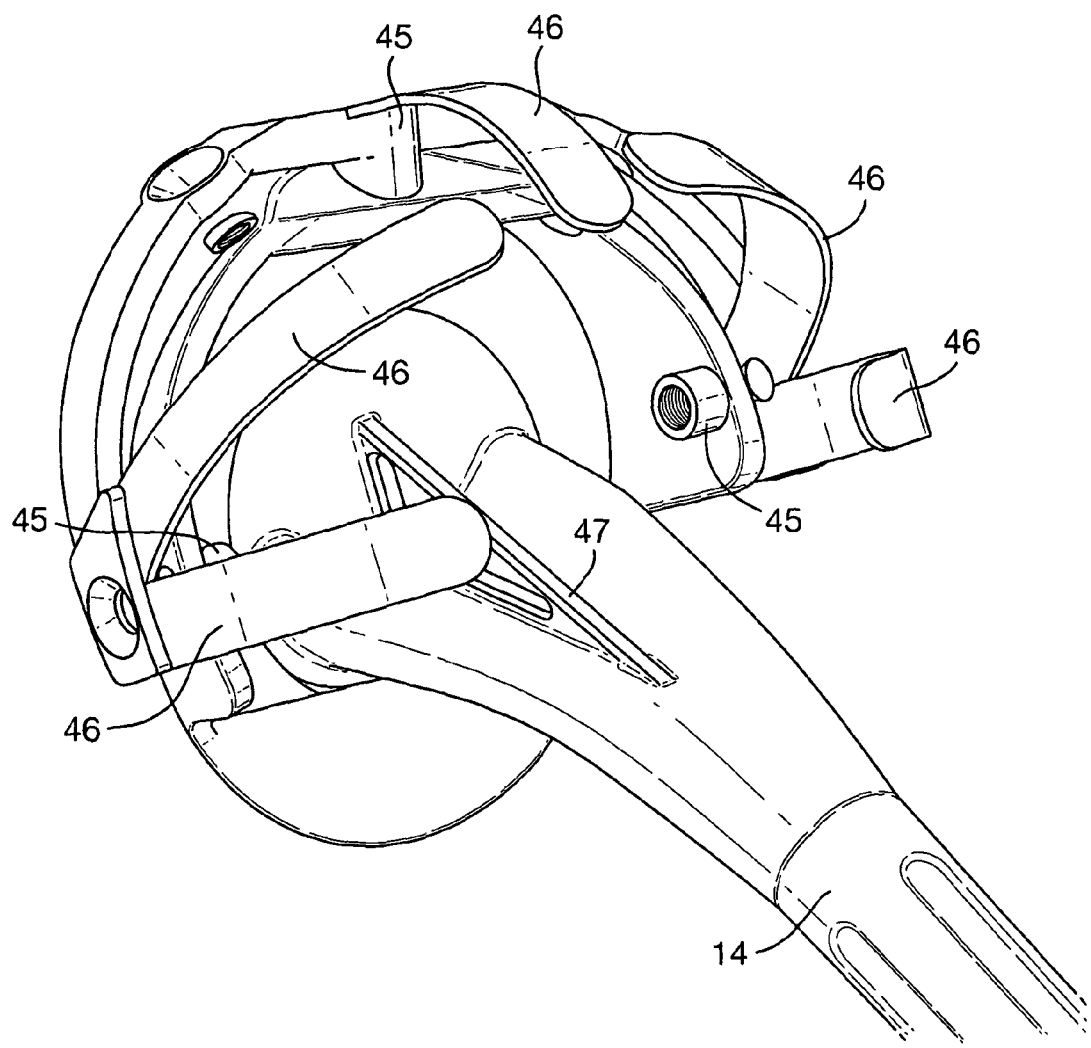
FIG. 6 shows the underside of the head of the prosthesis.

FIG. 6 shows the underside of the head of the prosthesis in more detail. In this example, the two side anchorage points have two arms 46, whereas the central anchorage point has only one. FIG. 6 also shows a strengthening rib 47 on the shaft where it connects to the base of the head.

Figure 7:
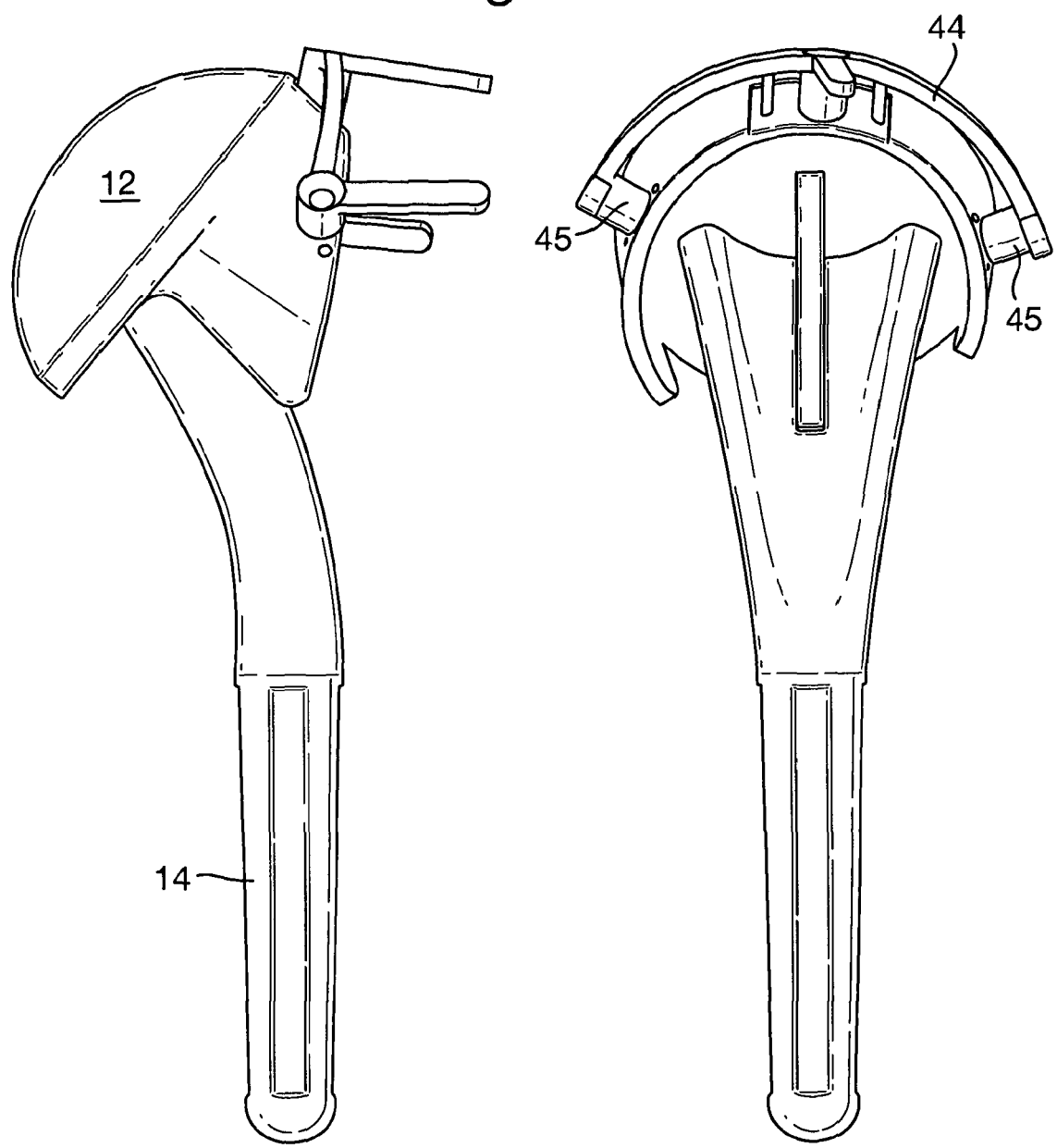
FIG. 7 shows design tool images of a prosthesis of the invention.

FIG. 7 shows design tool images of a prosthesis of the invention. These images correspond to those of FIG. 5, but with the bone image removed.

Figure 8:
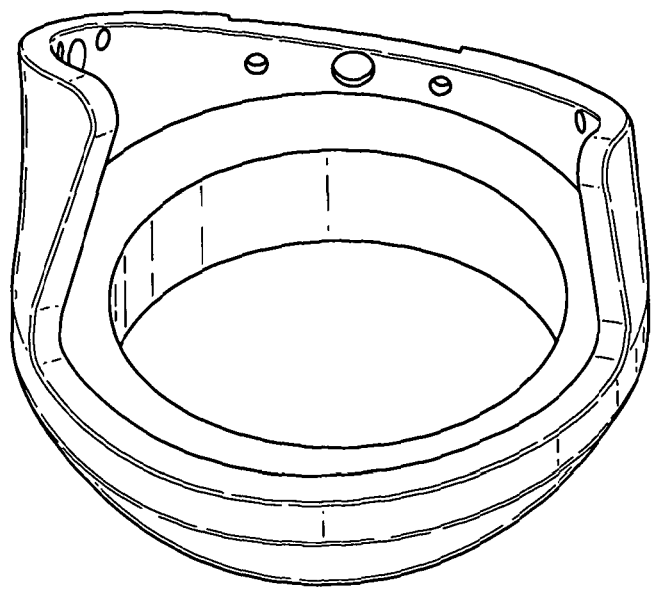
FIG. 8 shows a design tool image of the head and flange of the prosthesis of the invention.

FIG. 8 shows a design tool image of the head and flange of the prosthesis of the invention, to show more clearly the flange shape.

Figure 9:
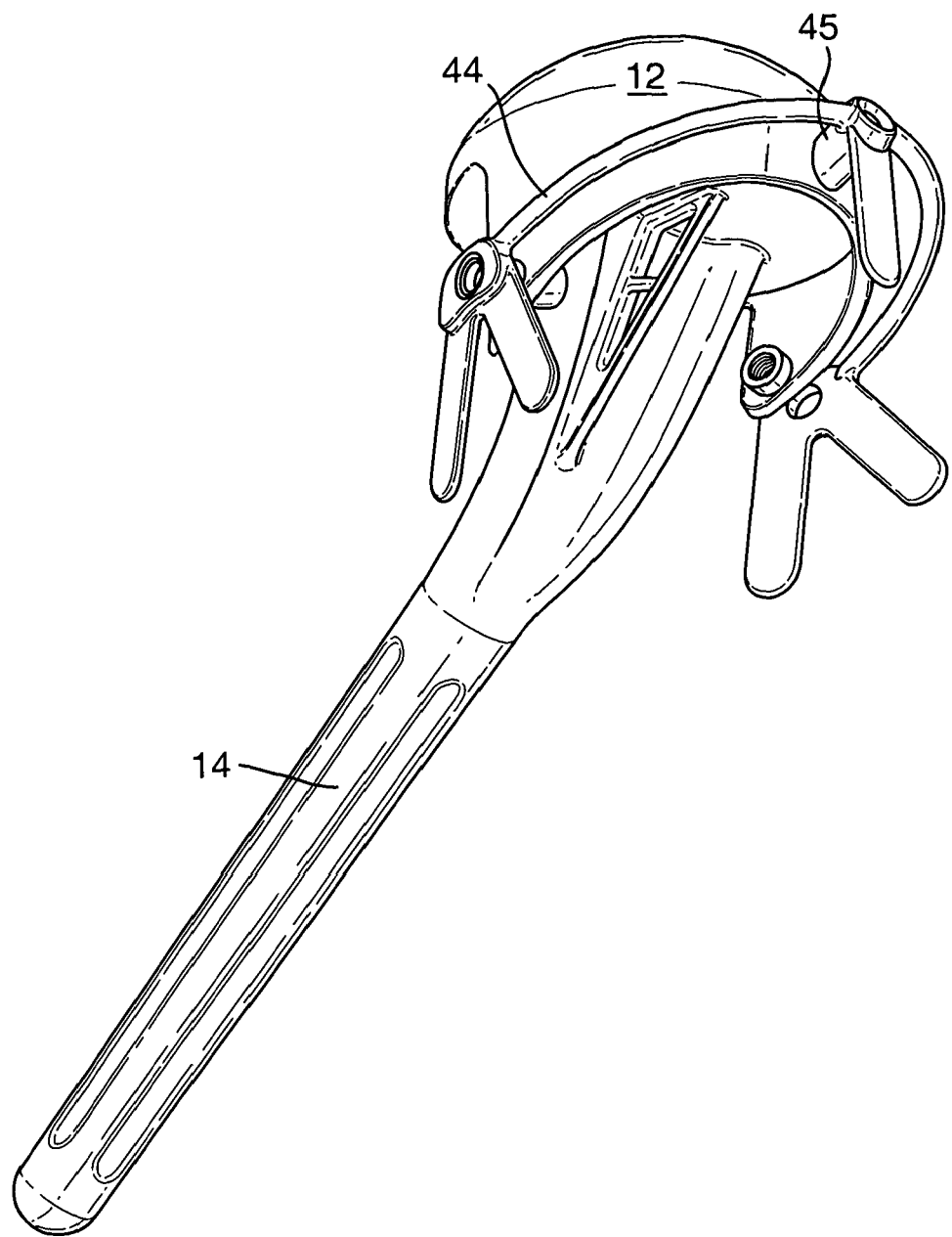
FIG. 9 shows a perspective design tool image of a prosthesis of the invention.

FIG. 9 shows a perspective design tool image of a prosthesis of the invention.

The concepts of the invention described above can be applied to fracture repair or repair of torn tendons. Thus, the inventive concepts can apply to a system for repairing degenerative tears (in the absence of fracture), or repairing fractures without any form of head replacement, as well as to tuberosity fragment repair in shoulder joint replacement procedures.

Figure 10:
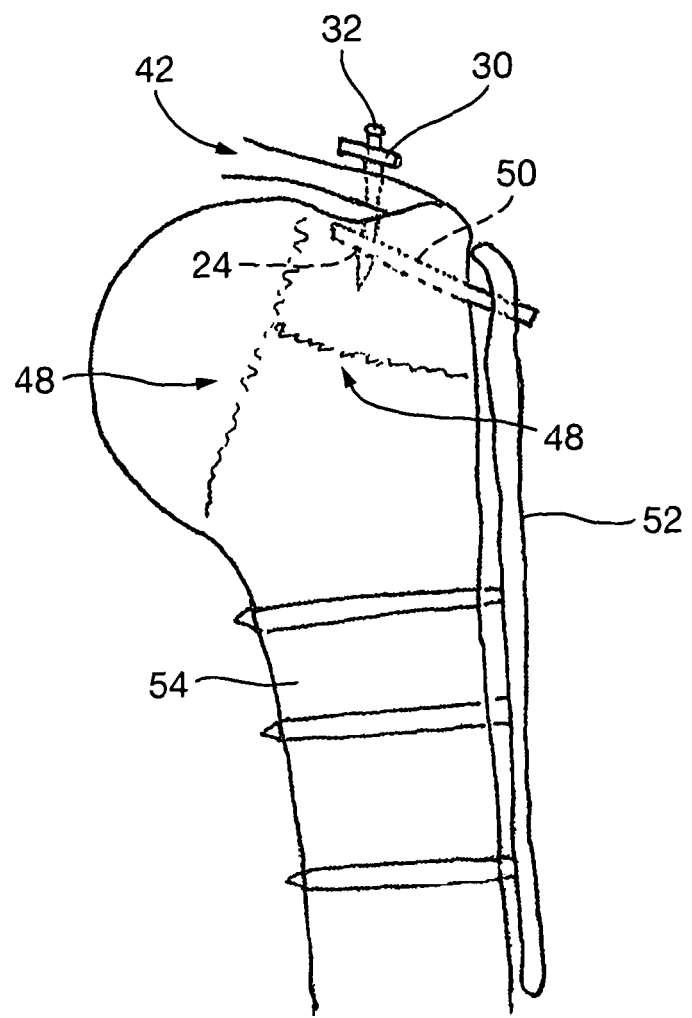
FIG. 10 shows the concepts of the invention applied to a fracture repair arrangement in a first view.

FIG. 10 shows the concepts of the invention applied to a fracture repair arrangement, in a first view. The same concept of providing an anatomical set of anchorage points is used, and with the use of clamps to secure the tendons. Fracture lines are shown as 48.

The support structure comprises a set of rods 50 for insertion into the bone of the joint, the rods 50 having one of the anchorage points 24 at the insertion end, wherein the inserted rods define the support surface located within the joint. Thus, a similar set of anchorage points is defined as for the prosthesis example, and the same method of direct connection (for example with screws 32) of the clamps 30 to the anchorage points 24 is used. However, the surface defined by the anchorage points lies within the joint head, and the surface against which the tendons are pressed is the surface of the existing bone joint.

The rods 50 are connected to a support plate 52 for connection to the bone shaft 54 leading to the joint. The rods can have the form of a rectangular plate that is fixed into the support plate 52. They protrude into the bone where a space for them has been made by a specialised awl, and a reception thread forms the anchorage point.

Figure 11:
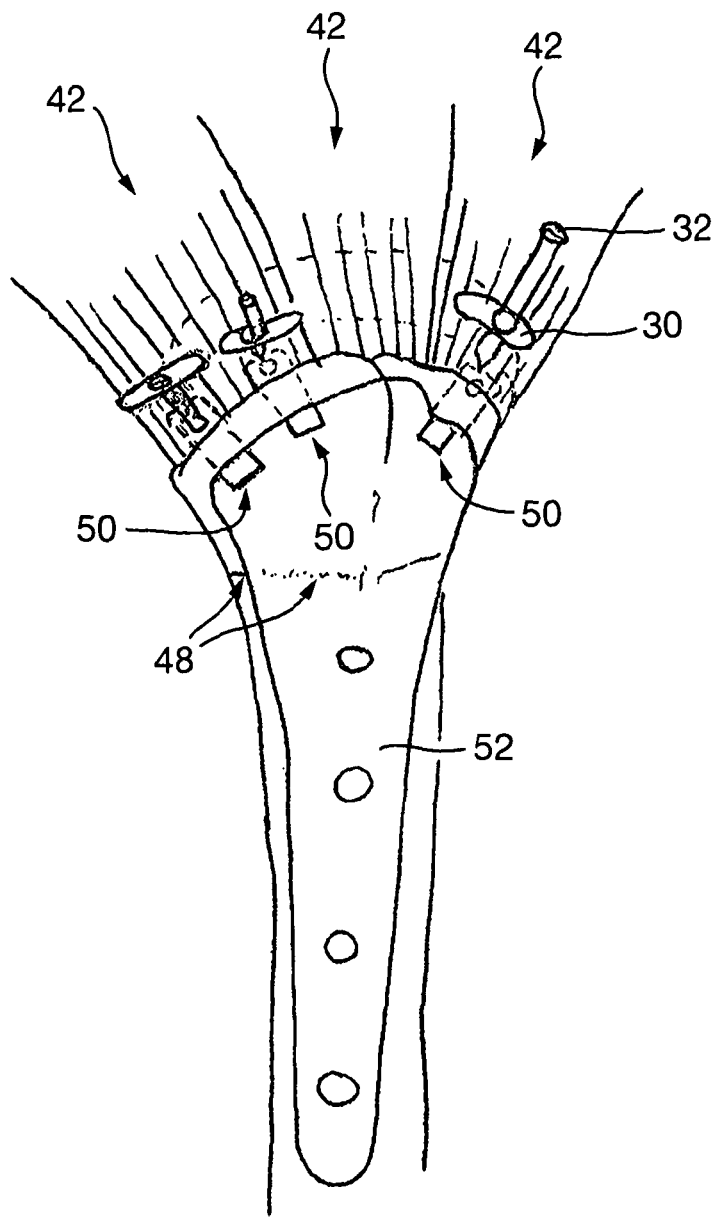
FIG. 11 shows the concepts of the invention applied to a fracture repair arrangement in a second view.

FIG. 11 shows the apparatus of FIG. 10 in a second view, to show the support plate 52 more clearly.

As explained above, the clamping of the tendons should not be so tight as to risk damage to the tendon, but should create a small enough gap to prevent bone fragments slipping through. Thus, the same 4 mm gap between the surface of the bone and the clamp 30 is provided, by any suitable spacer, such as a collar around the anchor 32.

Figure 12:
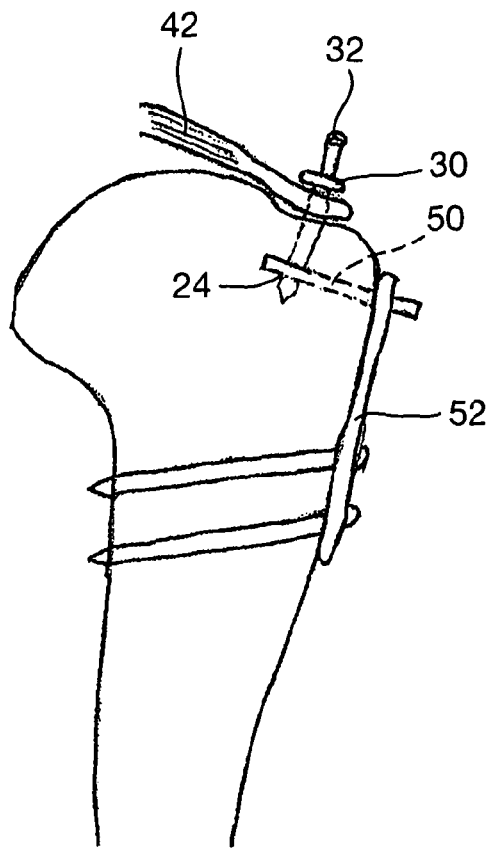
FIG. 12 shows the concepts of the invention applied to a tendon repair arrangement in a first view.
Figure 13:
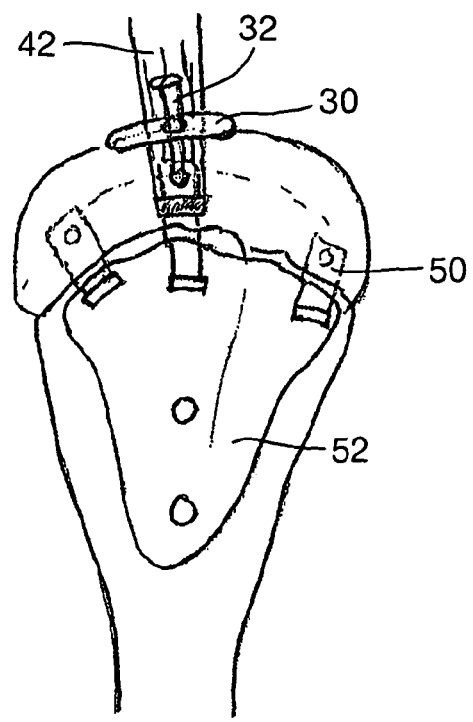
FIG. 13 shows the concepts of the invention applied to a tendon repair arrangement in a second view.

The same arrangement of FIGS. 10 and 11 can be used for tendon repair, although the support plate will require less extensive connection to the bone shaft, as shown in FIGS. 12 and 13 (which correspond to FIGS. 10 and 11).

In this case, there is no need for a deliberate gap (the 4 mm gap explained above) as there is no bony fragment attached.

The fracture repair version of FIGS. 10 and 11 uses a support plate 52 and a set of rods 50 to reposition and retain the fractured components while the bone fractures heal.

Traditional methods of fixing fractures of the proximal humerus (as opposed to excising the native head and replacing it with a prosthesis) also involve using metallic nails that pass down the humeral canal, and plates that seat on the outside of the bone. Traditionally the fracture elements have been divided into 4 parts: the humeral shaft, the fractured head, the lesser tuberosity and the greater tuberosity. Although in young people the intervening bone connecting these parts is reasonably substantial, in the elderly the bone is of poor quality, so that when the fracture occurs, reconstruction of the parts is accompanied by a large hole or void, representing the poor quality or essentially the absence of such intervening bone. This void is sometimes termed the "$5^{th}$ Part" or "$5^{th}$ element" of such fractures.

When fixation rather than replacement is contemplated this poses a problem. With replacement, the anatomical relationship between the shaft and the prosthetic head is secure and set in steel. With fixation, however, it is difficult to control the humeral head, particularly if this head is no more than an "eggshell" and screws or nails attempt to hold the head position . Essentially such screws will traverse the $5^{th}$ element void of bone and then have purchase in only 1.5 cm of head.

Thus, loss of position is common. Two recent advances help to overcome this, but are not without complications or failure. They are the use of bone cement to fill the $5^{th}$ element void, and the use of locking screws on the plate. However the use of bone cement can lead to leakage into undesirable areas and can be difficult to apply. Appropriate filling of the void is not always obtained. The passage of screws through the cement is also a potential problem.

The locking screws also have a disadvantage, as being locked into the plate, the opposite end of the screw is inclined to force through the weak bone of the head and protrude into the joint.

These issues mean that the plate and screw fracture repair approach (both the traditional approach and that of FIGS. 10 and 11) is more appropriate for young patients.

Figure 14:
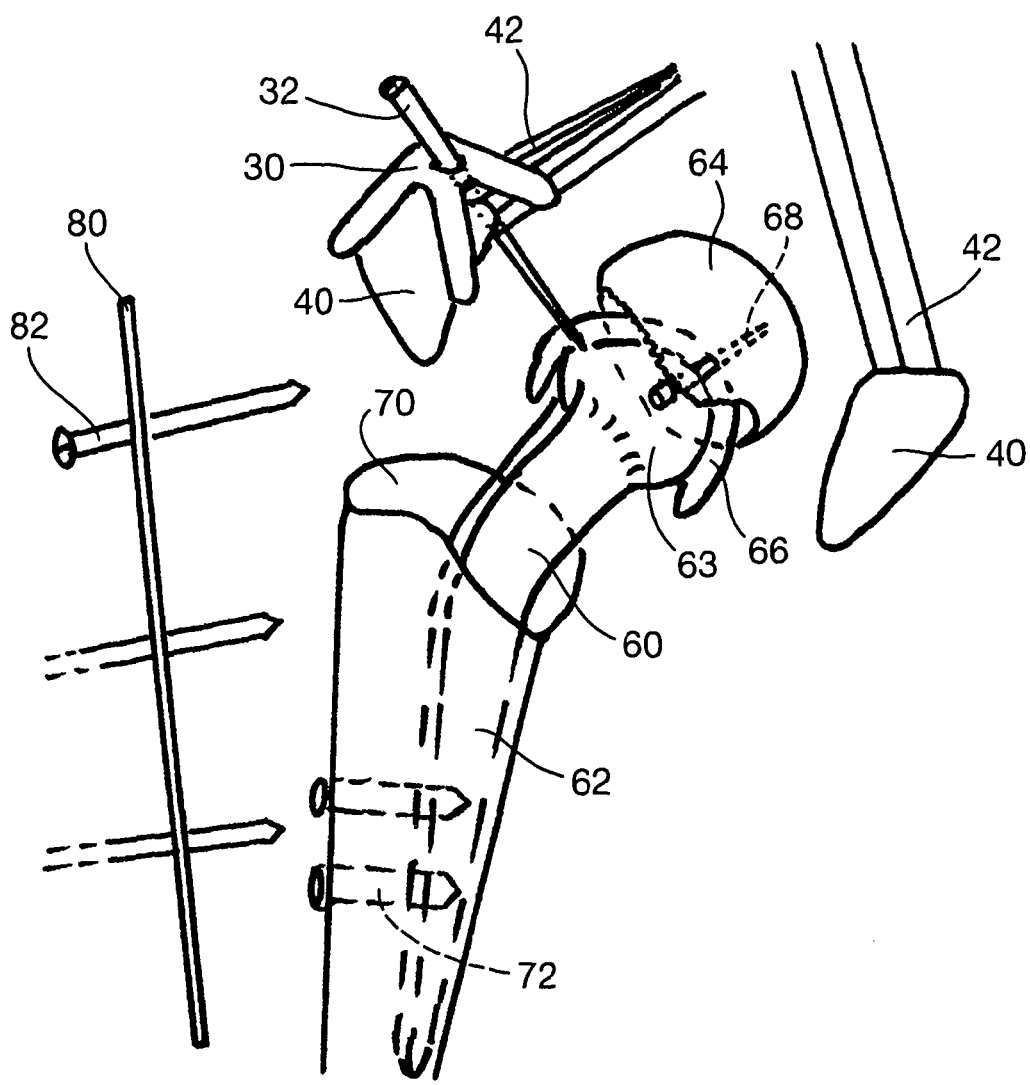
FIG. 14 shows a second version of fracture repair arrangement using the concepts of the invention.

An alternative approach to fracture repair is explained with reference to FIG. 14, and which is suitable for elderly patients having the particular issues described above. It uses the same concept of anatomical positioning of fixing points as will become apparent from the description below.

An absorbable implant 60 has a shaft 62 and a diminutive head 63 which fits inside the native fractured head 64. The absorbable implant is plastic, for example made of bio-absorbable calcified triglyceride (BCT) (known as Kryptonite bone cement). It is constructed from a computer tomography scan of the proximal humerus. Essentially the implant has the shape of the hemiarthroplasty of the prosthesis described above i.e. the proximal humerus minus the tuberosities. However, in addition, most of the prosthetic head is removed such that the remaining diminutive "head" can be inserted into the eggshell like native humeral head. The domed head is thus smaller, but the flange part, which has the anatomical insertion points against which the tuberosities are to be fixed, has the same design.

The native fractured head is reamed with a spherical reamer to accommodate the diminutive head 63, with a snug fit (a sphere within a sphere). The diminutive absorbable head also bears an absorbable skirt 66, again designed from computer tomography scans, to locate subjacent to the insertion points of the tendinous cuff into the tuberosities 40. Thus, the skirt is designed in the manner explained above for the prosthesis.

The fit between the diminutive absorbable head 63 and the native fractured head 64 is concentric and the hold between the two structures is augmented by absorbable screws 68.

In the fracture repair procedure the following steps are carried out.

(i) The absorbable prosthetic shaft 62 is placed into the native humeral shaft canal 70 where it occupies a position along the medial wall of the canal and is held there by screws 72 passed into the humeral shaft.

(ii) The native fractured humeral head 64 is reamed with a spherical reamer and the diminutive prosthetic head 63 introduced into it and secured with the absorbable screws 68.

(iii) The tuberosities are lowered onto the prosthetic skirt 66 and a low profile metal clamp 30 (of the form described above for the prosthesis, and hence given the same reference number) is secured by the screw 32 that traverses the tendon 42 and passes into the absorbable skirt 66.

The shape of the absorbable implant means that the tuberosities are laid on the absorbable prosthetic skirt with the same anatomical positioning as explained above in connection with the prosthesis. As with the prosthesis, the clamps may be constructed to create a fixed gap of 4 mm between themselves and the plastic skirt, and therefore again provide a trapdoor mechanism for holding the tuberosities.

A conventional metallic side plate 80 with screw 82 may be used to augment all aspects of this fixation.

There are numerous advantages to this system. In particular, the hold on the native head is likely to be stronger. The implant will be strong but slowly absorb and replace with normal bone over a period of 3 to 6 months. The implant will be fully absorbed over 6 to 9 months, at which time the bone healing renders the implant redundant.

The absorbable implant fixes the fractured shaft relative to the native humeral head, as well as fixing the tuberosities to the shaft. The procedure will be easier, empirical and direct and rely less on complicated X-ray screening in theatre and relies less on the passage of multiple screws. Ordinarily, a plate and screw fixation alone which passes through a void of fracture bone of little substance will give poor control on the head, particularly with rotation. As the diminutive head in this arrangement will mate with an identical reamed internal surface of the native head, a large surface area of hold will be applied to the head, that will require minimal augmentation via short absorbable screws to improve the hold.

The space occupied by the implant prevents collapse frequently seen in this area. The fact that the implant is absorbable means that screws from the clamp can be safely introduced in a variety of directions, without any aiming devices, the only requisite being that they engage the absorbable implant. This is an advantage over systems where the screw must engage a receptive hole in a metallic implant.

All materials used may vary in ways familiar to those skilled in the art. There may be multiple clamps, a varied number of screws as required.

This aspect of the invention provides a joint repair apparatus, comprising:

an absorbable implant comprising a head, which has a portion which is sized for reception in a hollowed fractured joint head, and a connection shaft, wherein the head also comprises a flange having a rim which represents the positions of the anatomical tendinous insertion points; and a securing clamp arrangement which connects to the flange with metallic (or absorbable) screws (preferably low profile), the securing clamp arrangement being arranged to clamp the tendons between the securing clamp arrangement and the underlying surface area of the flange.

Again, bearing means can be provided for defining a spacing between the clamp arrangement and the underlying surface area, thereby to trap any attached bony fragments that are too large to slip through the spacing. Further metal screws and a metal plate can be provided for securing the connection shaft to the bone shaft associated with the joint, if desired.

It can be seen from the above description that the elements of the system in all applications are:
- one or more metal surface areas that seat below or inferior to the anatomical positions of the rotator cuff (or tendon); and
- securing structures above the rotator cuff (or tendon) that compress the cuff against the aforementioned surface areas.

In the case of joint repair and tendon repair, the key features are:
- a support structure or firm surface area which comprises anchorage points, wherein the support structure is positioned subjacent to positions representing anatomical tendinous insertion points of the tendons; and
- a securing clamp arrangement which connects to the anchorage points with direct rigid connection devices, the securing clamp arrangement having a surface area larger than the connection devices, the securing clamp arrangement being arranged to clamp the tendons between the securing clamp arrangement and the underlying surface area and also trap any attached bony fragments that are too large to slip through the gap between the clamp and underlying surface area.

In this case, the support structure comprises a set of rods for insertion into the bone of the joint, the rods having one of the anchorage points at the insertion end, wherein the inserted rods define the support surface located within the joint. Thus, the surface area to which the connections are anchored are not part of a prosthesis, but are defined within the existing joint. Thus, the original joint is kept in place, but the anchorage points lie beneath the surface of the joint (since the tendons are to be in contact with the joint). Thus, the anchorage points lie within the bone, and this is achieved with the rod arrangement. The rods are preferably connected to a support plate for connection to the bone shaft leading to the joint.

The rigid fixing devices can comprise low profile locking screws. The clamps may have modifications on their underlying surfaces so as to compress, but not damage the tendons.

The components (clamps, screws, prosthesis head and shaft) will typically be metal but any material deemed suitable for insertion into the human body with the required strength can be used.

The desired anatomical positioning of the anchorage points is defined by the prosthesis itself, whereas for the tendon or fracture repair solution, it is the installed configuration of rods attached to the outside plate which defines the anatomical positioning. The concepts of the invention in the latter case thus apply particularly to the installed repair apparatus, as the installation provides the desired positioning of components.

The invention makes use of the positions of the anatomical tendinous insertion points of the tendons. These positions are essentially the same for all adults, with deviations according to bone size. For example, a single prosthesis design can be used for all adults, and the positions of the insertion points do no need to be define on a per-individual basis. It will be understood therefore that for positions to represent the anatomical tendinous insertion points, a general correspondence with human anatomy is meant, rather than a correspondence with the precise anatomy of a specific individual.

Various modifications will be apparent to those skilled in the art.

The invention claimed is:

1. A joint repair prosthesis, comprising:
a head for replacing the joint head and a connection shaft, wherein the head comprises a substantially domed portion and a flange positioned at an end region of the domed portion;
anchorage points provided on the flange, wherein the flange defines a support structure or firm surface area; and
a securing clamp arrangement which connects to the anchorage points with direct rigid connection devices, the securing clamp arrangement having a surface area larger than the connection devices, the securing clamp arrangement being arranged to clamp the tendons between the securing clamp arrangement and an underlying surface area, and bearing means for defining a spacing between the clamp arrangement and the underlying surface area, thereby to trap any attached bony fragments that are too large to slip through the spacing.

2. An apparatus as claimed in claim 1, wherein the direct connection devices comprise screws.

3. A prosthesis as claimed in claim 1, wherein the flange comprises a plurality of anchorage points.

4. A prosthesis as claimed in claim 1, wherein the securing clamp arrangement comprises a clamp for each anchorage point, each clamp comprising an elongate arm shaped to correspond to the shape of the flange thereby providing a compression surface against the flange.

5. A prosthesis as claimed in claim 4, wherein each clamp comprises an extension arm which extends away from the flange, wherein the extension arms of the clamps together define a cage structure.

6. A prosthesis as claimed in claim 5, wherein the elongate arms are connected together to define a web.

7. A prosthesis as claimed in claim 6, wherein the anchorage points are positioned along the web.

8. A prosthesis as claimed in claim 1, wherein the means for defining a spacing comprises a spacer associated with at least one of the anchorage points.

9. A prosthesis as claimed in claim 8, wherein the means for defining a spacing comprises a spacer associated with each anchorage point.

10. A prosthesis as claimed in claim 1, comprising a shoulder prosthesis, wherein the width of the flange is in the region of 1 mm to 8 mm in the lesser tuberosity region and up to a maximum of between 8 mm and 25 mm in the greater tuberosity region or so as to replicate the anatomical bony structure in this region.

11. A prosthesis as claimed in claim 1, wherein the shaft is plastic, and the prosthesis is a trial prosthesis.

12. A prosthesis as claimed in claim 1, wherein the flange has a width which varies around the domed portion such that a rim of the flange away from the domed portion represents the positions of the anatomical tendinous insertion points and wherein the support structure or firm surface area is positioned subjacent to positions representing the anatomical tendinous insertion points of the tendons.

* * * * *